US009422411B2

(12) United States Patent
Sahouani et al.

(10) Patent No.: US 9,422,411 B2
(45) Date of Patent: Aug. 23, 2016

(54) REACTION MIXTURE, POROUS PARTICLES AND METHODS OF MAKING

(71) Applicant: 3M INNOVATIVE PROPERTIES COMPANY, St. Paul, MN (US)

(72) Inventors: Hassan Sahouani, Hastings, MN (US); Petra L. Kohler Riedi, Minneapolis, MN (US); Semra Colak Atan, Saint Louis Park, MN (US); Steven P. Swanson, Blaine, MN (US); Yongshang Lu, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/891,585

(22) PCT Filed: May 13, 2014

(86) PCT No.: PCT/US2014/037788
§ 371 (c)(1),
(2) Date: Nov. 16, 2015

(87) PCT Pub. No.: WO2014/186328
PCT Pub. Date: Nov. 20, 2014

(65) Prior Publication Data
US 2016/0068651 A1    Mar. 10, 2016

Related U.S. Application Data

(60) Provisional application No. 61/824,412, filed on May 17, 2013.

(51) Int. Cl.
| | |
|---|---|
| A61K 9/26 | (2006.01) |
| C08J 9/28 | (2006.01) |
| C08F 2/30 | (2006.01) |
| C08F 220/12 | (2006.01) |
| C08J 9/16 | (2006.01) |
| A01N 25/10 | (2006.01) |
| A01N 47/44 | (2006.01) |
| A61K 8/02 | (2006.01) |
| A61K 8/81 | (2006.01) |
| A61Q 19/00 | (2006.01) |
| C09D 7/12 | (2006.01) |

(52) U.S. Cl.
CPC . *C08J 9/28* (2013.01); *A01N 25/10* (2013.01); *A01N 47/44* (2013.01); *A61K 8/0279* (2013.01); *A61K 8/8164* (2013.01); *A61Q 19/00* (2013.01); *C08F 2/30* (2013.01); *C08F 220/12* (2013.01); *C08J 9/16* (2013.01); *C08J 9/286* (2013.01); *C09D 7/1291* (2013.01); *C08J 2201/04* (2013.01); *C08J 2205/024* (2013.01); *C08J 2207/10* (2013.01); *C08J 2333/14* (2013.01); *C08J 2333/24* (2013.01); *C08J 2335/02* (2013.01); *C08J 2347/00* (2013.01)

(58) Field of Classification Search
USPC ........................ 424/489, 497, 501
See application file for complete search history.

(56) References Cited

U.S. PATENT DOCUMENTS

| | | |
|---|---|---|
| 3,890,269 A | 6/1975 | Martin |
| 3,921,636 A | 11/1975 | Zaffaroni |
| 4,303,736 A | 12/1981 | Torobin |
| 4,661,577 A | 4/1987 | Jo Lane |
| 4,690,825 A | 9/1987 | Won |
| 4,743,545 A | 5/1988 | Torobin |
| 4,923,894 A | 5/1990 | Kanda |
| 5,026,890 A | 6/1991 | Webb et al. |
| 5,045,569 A | 9/1991 | Delgado |
| 5,190,775 A | 3/1993 | Klose |
| 5,214,119 A | 5/1993 | Leir |
| 5,276,122 A | 1/1994 | Aoki |
| 5,292,835 A | 3/1994 | Jahns |
| 5,316,774 A | 5/1994 | Eury |
| 5,461,134 A | 10/1995 | Leir |
| 5,512,650 A | 4/1996 | Leir |
| 5,554,686 A | 9/1996 | Frisch, Jr. |
| 5,888,930 A | 3/1999 | Smith |
| 5,908,896 A | 6/1999 | Mayer |
| 6,013,286 A | 1/2000 | Klose |
| 6,355,759 B1 | 3/2002 | Sherman |
| 6,406,719 B1 | 6/2002 | Farrar |
| 6,407,195 B2 | 6/2002 | Sherman |
| 6,441,118 B2 | 8/2002 | Sherman |

(Continued)

FOREIGN PATENT DOCUMENTS

| | | |
|---|---|---|
| EP | 0870540 | 10/1998 |
| EP | 1947121 | 7/2008 |

(Continued)

OTHER PUBLICATIONS

Anderl, "Role of Antibiotic Penetration Limitation in *Klebsiella pneumoniae* Biofilm Resistance to Ampicillin and Ciprofloxacin", Antimicrobial Agents and Chemotherapy, Jul. 2000, vol. 44, No. 7, pp. 1818-1824.

Barrett, "The Determination of Pore Volume and Area Distributions in Porous Substances", J. Am. Chem. Soc., Jan. 1951, vol. 73, pp. 373-380.

CASTORWAX®, Technical Data Sheet, Vertellus Performance Materials, Inc., Nov. 2006, 1 page.

Gokmen, "Porous polymer particles—A comprehensive guide to synthesis, characterization, functionalization and applications", Progress in Polymer Science, 2012, vol. 37, pp. 365-405.

Liang, "Synthesis of a Novel Porous Polymer/Ceramic Composite Material by Low-Temperature Atomic Layer Deposition", Chem. Mater., Oct. 2007, vol. 19, No. 22, pp. 5388-5394.

(Continued)

*Primary Examiner* — Pancham Bakshi
(74) *Attorney, Agent, or Firm* — Jean A. Lown

(57) ABSTRACT

Porous polymeric particles are provided that can be hydrophilic or hydrophobic. The porous polymeric particles can be used for the storage and delivery of various active agents or for moisture management. Reaction mixtures for forming the porous polymeric particles, methods of making the porous polymeric particles, and articles containing the porous polymeric particles are also provided.

5 Claims, 2 Drawing Sheets

(56) References Cited

U.S. PATENT DOCUMENTS

| | | |
|---|---|---|
| 6,720,007 B2 | 4/2004 | Walt |
| 6,746,684 B2 | 6/2004 | Kitagaki |
| 6,835,397 B2 | 12/2004 | Lee |
| 6,846,893 B1 | 1/2005 | Sherman |
| 7,153,924 B2 | 12/2006 | Kuepfer |
| 7,371,464 B2 | 5/2008 | Sherman |
| 7,491,409 B1 | 2/2009 | Meers |
| 2003/0199633 A1 | 10/2003 | Leon |
| 2005/0202096 A1 | 9/2005 | Li |
| 2007/0148474 A1 | 6/2007 | Leir |
| 2009/0068256 A1 | 3/2009 | Meers |
| 2009/0176098 A1 | 7/2009 | Masuda |
| 2009/0246279 A1 | 10/2009 | Kong |
| 2010/0104647 A1 | 4/2010 | Ting |
| 2011/0086100 A1 | 4/2011 | Attia |
| 2011/0123456 A1 | 5/2011 | Pandit |
| 2014/0309314 A1 | 10/2014 | Sahouani |

FOREIGN PATENT DOCUMENTS

| | | |
|---|---|---|
| WO | WO 97/40103 | 10/1997 |
| WO | WO 01/54900 | 8/2001 |
| WO | 2006/133519 | 12/2006 |
| WO | WO 2006/135519 | 12/2006 |
| WO | WO 2007/146722 | 12/2007 |
| WO | WO2007/146722 A1 * | 12/2007 ............ C08F 20/26 |
| WO | WO 2009/061759 | 5/2009 |
| WO | WO 2012/082582 | 6/2012 |
| WO | WO 2012/134679 | 10/2012 |
| WO | WO 2012/142240 | 10/2012 |
| WO | WO 2013/166020 | 11/2013 |
| WO | WO 2014/022453 | 2/2014 |
| WO | WO 2014/186336 | 11/2014 |
| WO | WO 2015/094710 | 6/2015 |
| WO | WO 2015/095100 | 6/2015 |

OTHER PUBLICATIONS

Stipanovic, "Microparticle Dispensers for the Controlled Release of Insect Pheromones", J. Agric. Food Chem., Apr. 2004, vol. 52, No. 8, pp. 2301-2308.

International Search Report for PCT International Application No. PCT/US2014/037788, mailed on Aug. 21, 2014, 3 pages.

* cited by examiner

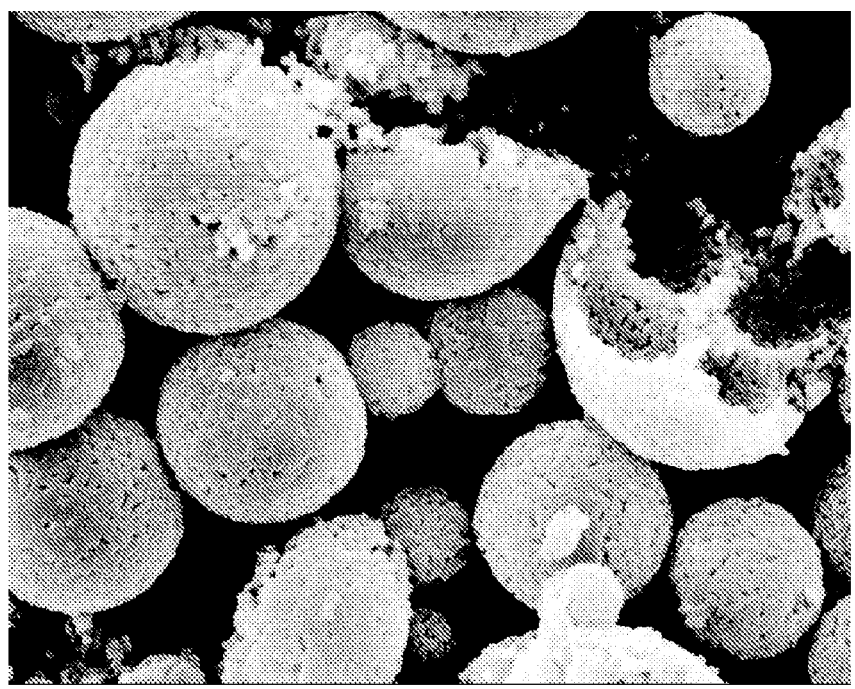
*FIG. 2*  10 μm
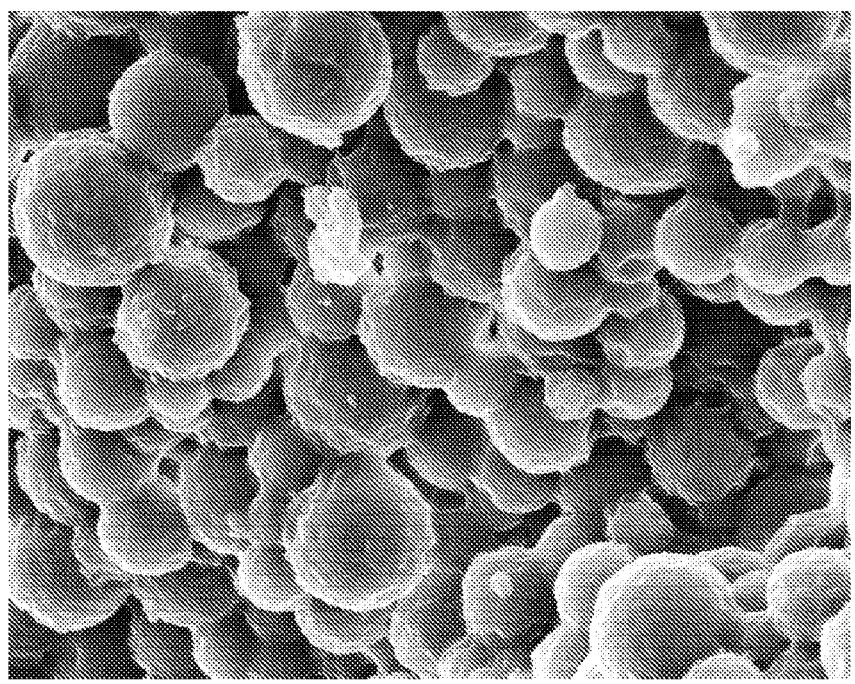
*FIG. 3*  10 μm

REACTION MIXTURE, POROUS PARTICLES AND METHODS OF MAKING

CROSS REFERENCE TO RELATED APPLICATIONS

This application is a national stage filing under 35 U.S.C. 371 of PCT/US2014/037788, filed May 13, 2014, which claims priority to U.S. Provisional Application No. 61/824,412, filed May 17, 2013, the disclosure of which is incorporated by reference in its/their entirety herein.

FIELD

Porous polymeric particles are provided. The polymeric particles can be used for the storage and delivery of various active agents or for moisture management.

BACKGROUND

Methods for delivering active agents are of great interest. Various particles have been developed for storage and delivery of various active agents. Some particles are inorganic as described, for example, in Patent Application Publication WO 2006/135519 A1 (Finnie et al.). Other particles have a polymeric shell surrounding a hollow core that can be filed with active agents. Such particles are described, for example, in U.S. Patent Application Publication 2010/0104647 A1 (Ting) and U.S. Patent Application Publication 2011/0123456 (Pandidt et al.). Still other particles are hydrogels that swell when placed in contact with an active agent. Such hydrogels are described, for example, in WO 2007/146722 (Wright et al.).

SUMMARY

Polymeric particles are provided that are porous and that can be used for the storage and delivery of various active agents or for moisture management. Reaction mixtures used to form the polymeric particles, methods of making the polymeric particles, and articles containing the polymeric particles are described. The porous polymeric particles can be in the form of hollow beads.

In a first aspect, a reaction mixture is provided that includes (a) a first phase and (b) a second phase dispersed in the first phase, wherein a volume of the first phase is greater than a volume of the second phase. The first phase contains (i) a compound of Formula (I)

$$HO[-CH_2-CH(OH)-CH_2-O]_n-H \qquad (I)$$

where the variable n is an integer equal to at least 1 and (ii) a nonionic surfactant. The second phase contains (i) a monomer composition comprising a monomer of Formula (II)

$$CH_2=C(R^1)-(CO)-O[-CH_2-CH_2-O]_p-\\(CO)-C(R^1)=CH_2 \qquad (II)$$

where the variable p is an integer equal to at least 1 and where $R^1$ is hydrogen or methyl, and (ii) a poly(propylene glycol) having a weight average molecular weight of at least 500 grams/mole.

In a second aspect, a porous polymeric particle is provided that is formed from a polymerized product of a reaction mixture. The reaction mixture includes (a) a first phase and (b) a second phase dispersed in the first phase, wherein a volume of the first phase is greater than a volume of the second phase. The first phase contains (i) a compound of Formula (I)

$$HO[CH_2-CH(OH)-CH_2-O]_n-H \qquad (I)$$

where the variable n is an integer equal to at least 1 and (ii) a nonionic surfactant. The second phase contains (i) a monomer composition comprising a monomer of Formula (II)

$$CH_2=C(R^1)-(CO)-O[-CH_2-CH_2-O]_p-\\(CO)-C(R^1)=CH_2 \qquad (II)$$

where the variable p is an integer equal to at least 1 and where $R^1$ is hydrogen or methyl, and (ii) a poly(propylene glycol) having a weight average molecular weight of at least 500 grams/mole. The poly(propylene glycol) is removed from the polymerized product to provide the porous polymeric particle.

In a third aspect, an article is provided that contains 1) a substrate and 2) porous polymeric particles distributed on a surface of the substrate, throughout the substrate, or a combination thereof. The porous polymeric particles contain a polymerized product of a reaction mixture that includes (a) a first phase and (b) a second phase dispersed in the first phase, wherein a volume of the first phase is greater than a volume of the second phase. The first phase contains (i) a compound of Formula (I)

$$HO[CH_2-CH(OH)-CH_2-O]_n-H \qquad (I)$$

where the variable n is an integer equal to at least 1 and (ii) a nonionic surfactant. The second phase contains (i) a monomer composition comprising a monomer of Formula (II)

$$CH_2=C(R^1)-(CO)-O[-CH_2-CH_2-O]_p-\\(CO)-C(R^1)=CH_2 \qquad (II)$$

where the variable p is an integer equal to at least 1 and where $R^1$ is hydrogen or alkyl, and (ii) a poly(propylene glycol) having a weight average molecular weight of at least 500 grams/mole. The poly(propylene glycol) is removed from the polymerized product to provide the porous polymeric particles.

In a fourth aspect, a method of making a porous polymeric particle is provided. The method includes preparing a first phase that contains (i) a compound of Formula (I)

$$HO(-CH_2-CH(OH)-CH_2-O)_n-H \qquad (I)$$

where the variable n is an integer equal to at least 1 and (ii) a nonionic surfactant. The method further includes forming a second phase, wherein a volume of the first phase is greater than a volume of the second phase. The second phase contains (i) a monomer composition comprising a monomer of Formula (II)

$$CH_2=C(R^1)-(CO)-O[-CH_2-CH_2-O]_p-\\(CO)-C(R^1)=CH_2 \qquad (II)$$

where the variable p is an integer equal to at least 1 and where $R^1$ is hydrogen or alkyl, and (ii) a poly(propylene glycol) having a weight average molecular weight of at least 500 grams/mole. The method still further includes providing a reaction mixture by dispersing the second phase in the first phase, curing the monomer composition within the reaction mixture to form a polymerized product, and then removing the poly(propylene glycol) from the polymerized product to form the porous polymer particle.

BRIEF DESCRIPTION OF THE DRAWINGS

FIG. 2 is a scanning electron micrograph of comparative polymeric particles prepared in Comparative Example A.

FIG. 3 is a scanning electron micrograph of polymeric particles prepared in Example 1 and then broken to view an internal portion of the polymeric particle.

DETAILED DESCRIPTION

Figure 1:
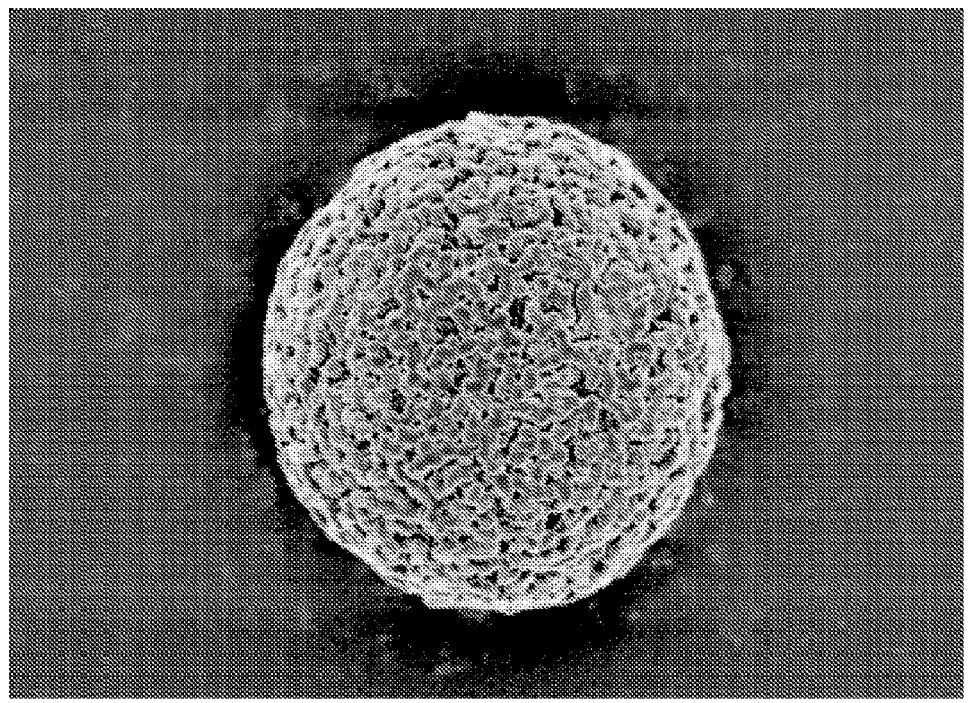
FIG. 1 is a scanning electron micrograph of a polymeric particle prepared in Example 1.

Porous polymeric particles are provided. That is, the polymeric particles have voids or free volume. The porous polymeric particles have pores on its outer surface and/or channels into the interior region. In at least some embodiments, the porous polymeric particles are hollow. The porous polymeric particles can be used for the storage and delivery of various active agents or for moisture management. Reaction mixtures for forming the porous polymeric particles, articles containing the porous polymeric particles, and method of making the porous polymeric particles are also provided. The terms "porous polymeric particle" and "polymeric particle" are used interchangeably.

The porous polymeric particles can be loaded with an active agent (i.e., an active agent is positioned or loaded within the porous polymeric particles). Such polymeric particle containing an active agent can be referred to interchangeably as "loaded particles", "loaded polymeric particles" and "loaded porous polymeric particles". The active agent is not covalently bonded to the polymeric particles. Under suitable conditions, the active agent can be released (i.e., delivered) from the loaded polymeric particles.

As used herein, the terms "polymer" and "polymeric", and "polymeric material" are used interchangeably to refer to a homopolymer, copolymer, terpolymer, or the like.

As used herein, the term "and/or" means one or both. For example, the expression component A and/or component B refer to a component A alone, component B alone, or to both component A and component B.

The reaction mixture used to form the porous polymeric particle includes a first phase comprising a non-polymerizable medium and a second phase suspended in the first phase as droplets. The second phase includes at least a monomer of Formula (II) plus poly(propylene glycol) of a suitable size to function as a porogen. The polymerized product is washed to remove the poly(propylene glycol) to provide the porous polymeric particle.

In a first aspect, a reaction mixture is provided that can be used to provide porous polymeric particles. The reaction mixture includes a first phase and a second phase dispersed in the first phase with the volume of the first phase being greater than a volume of the second phase. That is, the first phase can be considered to be the continuous phase and the second phase can be considered to be the dispersed phase within the continuous phase. The first phase provides a non-polymerizable medium for suspending the second phase as droplets within the reaction mixture. The second phase droplets include a monomer composition that can undergo polymerization plus a porogen, which is poly(propylene glycol).

The first phase of the reaction mixture includes (i) a compound of Formula (I)

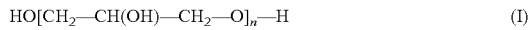

$$HO[CH_2-CH(OH)-CH_2-O]_n-H \qquad (I)$$

where the variable n is an integer equal to at least 1 and (ii) a nonionic surfactant. The first phase is typically formulated to provide a suitable viscosity and volume for dispersion of the second phase as droplets within the first phase. If the viscosity of the first phase is too high, it can be difficult to provide the requisite shear to disperse the second phase. If the viscosity is too low, however, it can be difficult to suspend the second phase and/or to form polymeric particles that are relatively uniform and well separated from each other.

Suitable compounds of Formula (I) typically have a value of n that is in a range of 1 to 20, in a range of 1 to 16, in a range of 1 to 12, in a range of 1 to 10, in a range of 1 to 6, or in a range of 1 to 4. In many embodiments, the compound of Formula (I) is glycerol where the variable n is equal to 1. Other example compounds of Formula (I) are diglycerol (n is equal to 2), polyglycerol-3 (n is equal to 3), polyglycerol-4 (n is equal to 4), or polyglycerol-6 (n is equal to 6). The polyglycerols, which can be referred to as polyglycerins, are often a mixture of materials with varying molecular weight (i.e., materials with different values for n). Polyglycerols, diglycerol, and glycerol are commercially available, for example, from Solvay Chemical (Brussels, Belgium) and Wilshire Technologies (Princeton, N.J., USA).

In addition to the compound of Formula (I), the first phase includes a nonionic surfactant. The nonionic surfactant increases the porosity on the surface of the final polymeric particles. The first phase is usually free or substantially free of an ionic surfactant that could interfere with the polymerization reaction of the monomers within the second phase. As used herein with reference to the ionic surfactant, the term "substantially free" means that no ionic surfactant is purposefully added to the first phase but may be present as a trace impurity in one of the other components in the first phase. Any impurity is typically present in an amount no greater than 0.5 weight percent, no greater than 0.1 weight percent, or no greater than 0.05 weight percent based on a total weight of the first phase.

Any suitable nonionic surfactant can be used in the first phase. The nonionic surfactant often has hydroxyl group or ether linkages (e.g., —$CH_2$—O—$CH_2$—) in one portion of the molecule that can hydrogen bond with other components of the reaction mixture. Suitable nonionic surfactants include, but are not limited to alkyl glucosides, alkyl glucamides, alkyl polyglucosides, polyethylene glycol alkyl ethers, block copolymers of polyethylene glycol and polypropylene glycol, and polysorbates. Examples of suitable alkyl glucosides include, but are not limited to, octyl glucoside (also referred to as octyl-beta-D-glucopyranoside) and decyl glucoside (also referred to as decyl-beta-D-glucopyranoside). Examples of suitable alkyl glucamides include, but are not limited to, octanoyl-N-methylglucamide, nonanoyl-N-methylglucamide, and decanoyl-N-methylglucamide. These surfactants can be obtained, for example, from Sigma Aldrich (St. Louis, Mo., USA) or Spectrum Chemicals (New Brunswick, N.J., USA). Examples of suitable alkyl polyglucosides include, but are not limited to, those commercially available from Cognis Corporation (Monheim, Germany) under the trade designation APG (e.g., APG 325) and those commercially available from Dow Chemical (Midland, Mich., USA) under the trade designation TRITON (e.g., TRITON BG-10 and TRITON CG-110). Examples of polyethylene glycol alkyl ethers include, but are not limited to, those commercially available under the trade designation BRIJ (e.g., BRIJ 58 and BRIJ 98) from Sigma Aldrich (St. Louis, Mo., USA). Examples of block copolymers of polyethylene glycol and polypropylene glycol include, but are not limited to, those commercially available under the trade designation PLURONIC from BASF (Florham Park, N.J., USA). Examples of polysorbates include, but are not limited, to those commercially available under the trade designation TWEEN from ICI American, Inc. (Wilmington, Del., USA).

The surfactant can be present in the first phase in any suitable amount. Often, the surfactant is present in an amount equal to at least 0.5 weight percent, at least 1 weight percent, or at least 2 weight percent based on a total weight of the first phase. The surfactant can be present in an amount up to 15 weight percent, up to 12 weight percent, or up to 10 weight percent based on a total weight of the first phase. For example, the surfactant is often present in the first phase in an amount in a range of 0.5 to 15 weight percent, in a range of 1 to 12 weight percent, in a range of 0.5 to 10 weight percent, or in a range of 1 to 10 weight percent based on the total weight of the first phase. The remainder of the first phase (the part of the first phase that is not surfactant) typically is a compound of Formula (I) or predominately the compound of Formula (I).

In some examples, the first phase can contain 0.5 to 15 weight percent surfactant and 85 to 99.5 weight percent compound of Formula (I), 1 to 12 weight percent surfactant and 88 to 99 weight percent compound of Formula (I), 0.5 to 10 weight percent surfactant and 90 to 99.5 weight percent compound of Formula (I), or 1 to 10 weight percent surfactant and 90 to 99 weight percent compound of Formula (I). The percent weights are based on a total weight of the first phase. In many examples, the first phase contains only the surfactant and the compound of Formula (I). In other examples, the only other material included in the first phase is optional organic solvent or optional water.

Optionally, water or an organic solvent that is miscible with the compound of Formula (I) can be present in the first reaction mixture. Suitable organic solvents include, for example, an alcohol such as methanol, ethanol, n-propanol, or isopropanol. The amount of any optional water or organic solvent is selected so that the desired viscosity of the first phase can be achieved. The amounts of the optional water or organic solvent is often no greater than 10 weight percent, no greater than 5 weight percent, or no greater than 1 weight percent based on the total weight of the first phase. If higher amounts of water are included, the porosity my decrease. In some embodiments, the first phase is free or substantially free of the optional water or organic solvent. As used herein with reference to the optional water or organic solvent, the term "substantially free" means that water or organic solvent is not purposely added to the first phase but may be present as an impurity in one of the other components in the first phase. For example, the amount of the optional water or organic solvent is less than 1 percent, less than 0.5 weight percent, or less than 0.1 weight percent based on a total weight of the first phase.

The reaction mixture includes a second phase dispersed in the first phase. The volume of the first phase is greater than the volume of the second phase. The volume of the first phase is sufficiently large compared to the volume of the second phase so that the second phase can be dispersed in the form of droplets within the first phase. Within each droplet, the monomer composition is polymerized to form a polymerized product. To form particles from the second phase, the volume ratio of the first phase to the second phase is typically at least 2:1. As the volume ratio increases (e.g., when the ratio is at least 3:1, at least 4:1, or at least 5:1), beads can be formed that have a relatively uniform size and shape. If the volume ratio is too large, however, the reaction efficiency is diminished (i.e., a smaller amount of polymeric particles are produced). The volume ratio is generally no greater than 25:1, no greater than 20:1, no greater than 15:1, or no greater than 10:1.

The second phase includes both a monomer composition plus a poly(propylene glycol) having a weight average molecular weight of at least 500 grams/mole. The polypropylene glycol functions as a porogen that gets partially entrained within the polymerized product as it is formed from the monomer composition. Because the polypropylene glycol has no polymerizable group, this material can be removed after formation of the polymerized product. Pores (i.e., void volume or free volume) are created when the previously entrained polypropylene glycol is removed. The polymeric particles resulting from the removal of the entrained polypropylene glycol are porous. In at least some embodiments, these porous polymeric particles have hollow centers. The presence of pores or the presence of both pores and hollow centers make the polymeric particles well suited for storage and delivery of various active materials or for moisture management applications.

The monomer composition within the second phase contains a first monomer of Formula (II)

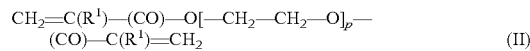

where the variable p is an integer equal to at least 1. In some embodiments, the variable p is an integer no greater than 30, no greater than 20, no greater than 16, no greater than 12, or no greater than 10. The number average molecular weight of the ethylene oxide portion of the monomer (i.e., the group —[CH$_2$CH$_2$—O]$_p$—) is often no greater than 1200 grams/mole, no greater 1000 grams/mole, no greater than 800 grams/mole, no greater than 1000 grams, mole, no greater than 600 grams/mole, no greater than 400 grams/mole, no greater than 200 grams/mole, or no greater than 100 grams/mole. The group R$^1$ is hydrogen or methyl. The monomer of Formula (II) in the second phase is typically not miscible with the first phase.

Suitable first monomers of Formula (II) are commercially available from Sartomer (Exton, Pa., USA) under the trade designation SR206 for ethylene glycol dimethacrylate, SR231 for diethylene glycol dimethacrylate, SR205 for triethylene glycol dimethacrylate, SR206 for tetraethylene glycol dimethacrylate, SR210 and SR210A for polyethylene glycol dimethacrylate, SR259 for polyethylene glycol (200) diacrylate, SR603 and SR344 for polyethylene glycol (400) di(meth)acrylate, SR252 and SR610 for polyethylene glycol (600) di(meth)acrylate, and SR740 for polyethylene glycol (1000) dimethacrylate.

In some embodiments, the first monomer of Formula (II) is the only monomer in the monomer composition of the second phase. In other embodiments, the first monomer of Formula (II) can be used in combination with at least one second monomer. The second monomer has a single ethylenically unsaturated group, which is often a (meth)acryloyl group of formula H$_2$C=CR$^1$—(CO)— where R$^1$ is hydrogen or methyl. Suitable second monomers are not miscible with the first phase but can be miscible or not miscible with the first monomer of Formula (II).

Some example second monomers are of Formula (III).

In this formula, group R$^1$ is hydrogen or methyl. In many embodiments, R$^1$ is hydrogen. Group Y is a single bond, alkylene, oxyalkylene, or poly(oxyalkylene). Group R$^2$ is a carbocyclic group or heterocyclic group. These second monomers tend to be miscible with the first monomer of Formula (I) in the second phase but are not miscible with the first phase.

As used herein, the term "alkylene" refers to a divalent group that is a radical of an alkane and includes groups that are linear, branched, cyclic, bicylic, or a combination thereof. As used herein, the term "oxyalkylene" refers to a divalent group that is an oxy group bonded directly to an alkylene group. As used herein, the term "poly(oxyalkylene)" refers to a divalent group having multiple oxyalkylene groups. Suitable Y alkylene and oxyalkylene groups typically have 1 to 20 carbon atoms, 1 to 16 carbon atoms, 1 to 12 carbon atoms, 1 to 10 carbon atoms, 1 to 8 carbon atoms, 1 to 6 carbon atoms, or 1 to 3 carbon atoms. The oxyalkylene is often oxyethylene or oxypropylene. Suitable poly(oxyalkylene) groups typically have 2 to 20 carbon atoms, 2 to 16 carbon atoms, 2 to 12 carbon atoms, 2 to 10 carbon atoms, 2 to 8 carbon atoms, 2 to 6 carbon atoms, or 2 to 4 carbon atoms. The poly(oxyalkylene) is often poly(oxyethylene), which can be referred to as poly(ethylene oxide) or poly(ethylene glycol).

Carbocyclic $R^2$ groups can have a single ring or can have multiple rings such as fused rings or bicylic rings. Each ring can be saturated, partially unsaturated, or unsaturated. Each ring carbon atom can be unsubstituted or substituted with alkyl groups. Carbocyclic groups often has 5 to 12 carbon atoms, 5 to 10 carbon atoms, or 6 to 10 carbon atoms. Examples of carbocyclic groups include, but are not limited to, phenyl, cyclohexyl, cyclopentyl, isobornyl, and the like. Any of these carbocyclic groups can be substituted with an alkyl group having 1 to 20 carbon atoms, 1 to 10 carbon atoms, 1 to 6 carbon atoms, or 1 to 4 carbon atoms.

Heterocyclic $R^2$ groups can have a single ring or multiple rings such as fused rings or bicylic rings. Each ring can be saturated, partially unsaturated, or unsaturated. The heterocyclic group contains at least one heteroatom selected from oxygen, nitrogen, or sulfur. The heterocyclic group often has 3 to 10 carbon atoms and 1 to 3 heteroatoms, 3 to 6 carbon atoms and 1 to 2 heteroatoms, or 3 to 5 carbon atoms and 1 to 2 heteroatoms. Examples of heterocyclic rings include, but are not limited to, tetrahydrofurfuryl.

Exemplary monomers of Formula (III) for use as the second monomer include, but are not limited to, benzyl(meth)acrylate, 2-phenoxyethyl(meth)acrylate (commercially available from Sartomer under the trade designation SR339 and SR340), isobornyl(meth)acrylate, tetrahydrofurfuryl (meth)acrylate (commercially available from Sartomer under the trade designation SR285 and SR203), 3,3,5-trimethylcyclohexyl(meth)acrylate (commercially available from Sartomer under the trade designation CD421 and CD421A), and ethoxylated nonyl phenol acrylate (commercially available from Sartomer under then trade designation SR504, CD613, and CD612).

Other example second monomers are alkyl(meth)acrylates of Formula (IV).

$$CH_2=CR^1-(CO)-O-R^3 \qquad (IV)$$

In Formula (IV), group $R^1$ is hydrogen or methyl. In many embodiments, $R^1$ is hydrogen. Group $R^3$ is a linear or branched alkyl having 1 to 20 carbon atoms, 1 to 10 carbon atoms, 1 to 6 carbon atoms, or 1 to 4 carbon atoms. These second monomers tend to be miscible with the first monomer of Formula (I) in the second phase but are not miscible with the first phase.

Examples of alkyl(meth)acrylates of Formula (IV) include, but are not limited to, methyl(meth)acrylate, ethyl(meth)acrylate, n-propyl(meth)acrylate, isopropyl(meth)acrylate, n-butyl(meth)acrylate, isobutyl(meth)acrylate, n-pentyl (meth)acrylate, 2-methylbutyl(meth)acrylate, n-hexyl(meth) acrylate, 4-methyl-2-pentyl(meth)acrylate, 2-ethylhexyl (meth)acrylate, 2-methylhexyl(meth)acrylate, n-octyl(meth) acrylate, isooctyl(meth)acrylate, 2-octyl(meth)acrylate, isononyl(meth)acrylate, isoamyl(meth)acrylate, n-decyl (meth)acrylate, isodecyl(meth)acrylate, 2-propylheptyl (meth)acrylate, isotridecyl(meth)acrylate, isostearyl(meth) acrylate, octadecyl(meth)acrylate, 2-octyldecyl(meth) acrylate, dodecyl(meth)acrylate, lauryl(meth)acrylate, and heptadecanyl(meth)acrylate.

In some embodiments, the only monomers in the monomer composition are the first monomer of Formula (II) and the second monomer of Formula (III), Formula (IV), or both. Any suitable amounts of the first monomer and second monomer can be used. The monomer composition often contains 10 to 90 weight percent of the first monomer and 10 to 90 weight percent of the second monomer based on a total weight of monomers in the monomer composition. For example, the second phase can contain 20 to 80 weight percent of the first monomer and 20 to 80 weight percent of the second monomer, 25 to 75 weight percent of the first monomer and 25 to 75 weight percent of the second monomer, 30 to 70 weight percent of the first monomer and 30 to 70 weight percent of the second monomer, or 40 to 60 weight percent of the first monomer and 40 to 60 weight percent of the second monomer based on a total weight of monomers in the monomer composition.

Depending on the final use of the polymeric particles prepared, it can be desirable to include at least one hydrophilic second monomer in the monomer composition. The addition of a hydrophilic second monomer tends to make the polymeric particles more suitable for storage and delivery of hydrophilic active agents or for moisture management applications. Additionally, the addition of a hydrophilic second monomer allows the polymeric particles to be dispersed in water more easily. Hydrophilic second monomers are selected so that they are not miscible with the first phase. These monomers may or may not be miscible with the first monomer of Formula (II).

Some example hydrophilic second monomers are hydroxyl-containing monomers of Formula (V).

$$CH_2=CR^1-(CO)-O-R^4 \qquad (V)$$

In Formula (V), group $R^1$ is hydrogen or methyl. In many embodiments, $R^1$ is hydrogen. Group $R^4$ is an alkyl substituted with one or more hydroxyl groups or a group of formula $-(CH_2CH_2O)_qCH_2CH_2OH$ where q is an integer equal to at least 1. The alkyl group typically has 1 to 10 carbon atoms, 1 to 6 carbon atoms, 1 to 4 carbon atoms, or 1 to 3 carbon atoms. The number of hydroxyl groups is often in a range of 1 to 3. The variable q is often in a range of 1 to 20, in a range of 1 to 15, in a range of 1 to 10, or in a range of 1 to 5. In many embodiments, the second monomer of Formula (IV) has a single hydroxyl group.

Example monomers of Formula (V) include, but are not limited to, 2-hydroxyethyl(meth)acrylate, 2-hydroxypropyl (meth)acrylate, 3-hydroxypropyl(meth)acrylate, and 4-hydroxybutyl(meth)acrylate), 2-hydroxylbutyl(meth)acrylate, polyethylene glycol mono(meth)acrylate (e.g., monomers commercially available from Sartomer (Exton, Pa., USA) under the trade designation CD570, CD571, and CD572), and glycol mono(meth)acrylate.

Other example hydrophilic second monomers are hydroxyl-containing monomers of Formula (VI).

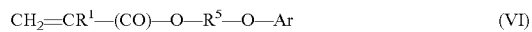

$$CH_2=CR^1-(CO)-O-R^5-O-Ar \qquad (VI)$$

In Formula (VI), group $R^1$ is hydrogen or methyl. In many embodiments, $R^1$ is hydrogen. Groups $R^5$ is an alkylene substituted with at least one hydroxyl group. Suitable alkylene groups often have 1 to 10 carbon atoms, 1 to 6 carbon atoms, or 1 to 4 carbon atoms. The alkylene group $R^5$ can be substituted with 1 to 3 hydroxyl groups but is often substituted with a single hydroxyl group. The group Ar is an aryl group having 6 to 10 carbon atoms. In many embodiments, the Ar group is phenyl. One example monomer of Formula (VI) is 2-hydroxy-2-phenoxypropyl(meth)acrylate.

If the second monomer is of Formula (V) or (VI), which are hydroxyl-containing monomers, the amount of this monomer that can be combined with the first monomer of Formula (II) is often no greater than 2 weight percent based on a total weight of monomers in the monomer composition. If greater than about 2 weight percent of the second monomer of Formula (V) or (VI) is used, the resulting polymeric particles tend to have diminished porosity.

Other hydrophilic monomers can be used as the second monomers in larger quantities than the second monomers of Formula (V) or (VI) without diminishing the porosity of the resulting polymeric particles. For example, sulfonyl-containing monomers of Formula (VII) or salt thereof can be included in the monomer composition along with the first monomer of Formula (II).

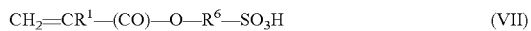

In Formula (VII), group $R^1$ is hydrogen or methyl. In many embodiments, $R^1$ is hydrogen. Group $R^6$ is an alkylene having 1 to 10 carbon atoms, 1 to 6 carbon atoms, or 1 to 4 carbon atoms. Examples of sulfonyl-containing monomers of Formula (VII) include, but are not limited to, sulfoethyl(meth)acrylate and sulfopropyl(meth)acrylate. The sulfonyl-containing monomers can be salts under some pH conditions. That is, monomer can have a negative charge and be associated with a positively charged counter ion. Example counter ions include, but are not limited to, alkali metals, alkaline earth metals, ammonium ions, and tetraalkyl ammonium ions.

If the second monomer is a sulfonyl-containing monomer of Formula (VII), the monomer composition can contain up to 20 weight percent of this monomer based on a total weight of monomers in the monomer composition. In some embodiments, the only monomers in the monomer composition are the first monomer of Formula (II) and the second monomer of Formula (VII). Any suitable amounts of the first monomer and second monomer can be used. The monomer composition often contains 80 to 99 weight percent of the first monomer of Formula (II) and 1 to 20 weight percent of the second monomer of Formula (VII) based on a total weight of monomers in the monomer composition. For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

In other embodiments, the monomer composition includes a first monomer of Formula (II) and two second monomers. The two second monomers are a sulfonyl-containing monomer, such as those of Formula (VII), and a hydroxyl-containing monomer, such as those of Formula (V) or (VI). When the hydroxyl-containing monomer is combined with a sulfonyl-containing monomer, higher amounts of the hydroxyl-containing monomer can be added to the monomer composition without substantially decreasing the porosity of the resulting polymeric particles. That is, the amount of the hydroxyl-containing monomer can be greater than 2 weight percent based on the weight of the monomers in the monomer composition. The monomer composition often contains 80 to 99 weight percent of the first monomer of Formula (II) and 1 to 20 weight percent of the second monomer, wherein the second monomer is a mixture of the sulfonyl-containing monomer and the hydroxyl-containing monomer. Up to 50 weight percent, up to 40 weight percent, up to 20 weight percent, or up to 10 weight percent of the second monomer can be the hydroxyl-containing monomer.

In still other embodiments, the monomer composition includes a first monomer of Formula (II) and two second monomers, which are a sulfonyl-containing monomer, such as those of Formula (VII), and a monomer of Formula (III). Such monomer compositions often contain 1 to 20 weight percent of the monomer of Formula (VII) and 80 to 99 weight percent of a mixture of the monomer of Formula (II) and the monomer of Formula (III). For example, the monomer compositions can contain 1 to 10 weight percent of the monomer of Formula (VII) and 90 to 99 weight percent of a mixture of the monomer of Formula (II) and the monomer of Formula (III) or can contain 1 to 5 weight percent of the monomer of Formula (VII) and 95 to 99 weight percent of a mixture of the monomer of Formula (II) and the monomer of Formula (III). These compositions can be advantageous because they can be used to load either hydrophobic or hydrophilic active agents.

In some more specific examples, the monomer composition can contain 1 to 20 weight percent of the monomer of Formula (VII), 1 to 98 weight percent of the monomer of Formula (II), and 1 to 98 weight percent of the monomer of Formula (III). In another example, the monomer composition can contain 1 to 20 weight percent of the monomer of Formula (VII), 5 to 95 weight percent of the monomer of Formula (II), and 5 to 95 weight percent of the monomer of Formula (III). In another example, the monomer composition contains 1 to 10 weight percent of the monomer of Formula (VII), 20 to 80 weight percent of the monomer of Formula (II), and 20 to 80 weight percent of the monomer of Formula (III). In yet another example, the monomer composition contains 1 to 10 weight percent of the monomer of Formula (VII), 30 to 70 weight percent of the monomer of Formula (II), and 30 to 70 weight percent of the monomer of Formula (III). In still another example, the monomer composition contains 1 to 10 weight percent of the monomer of Formula (VII), 40 to 60 weight percent of the monomer of Formula (II), and 40 to 60 weight percent of the monomer of Formula (III).

In these monomer compositions containing the monomers of Formulas (VII), (II), and (III), the amount of the monomer of Formula (VII) can be used to control the average size of the porous polymeric particle. For example, when about 5 weight percent of the monomer of Formula (VII) is included in the monomer composition, the resulting porous polymeric particles have an average diameter of approximately 10 micrometers. When about 1 weight percent of the monomer of Formula (VII) is included in the monomer composition, the resulting porous polymeric particles have an average diameter of approximately 3 micrometers.

Still other example second monomers are carboxyl-containing monomers that have a carboxylic acid group (—COOH) or salt thereof. Examples of these carboxyl-containing monomers include, but are not limited to, (meth)acrylic acid and carboxyalkyl(meth)acrylates such as 2-carboxyethyl(meth)acrylate, 3-carboxypropyl(meth)acrylate, and the like. The carboxyl-containing monomers can be salts under some pH conditions. That is, these monomer can have a negative charge and be associated with a positively charged counter ion. Example counter ions include, but are not limited to, alkali metals, alkaline earth metals, ammonium ions, and tetraalkyl ammonium ions.

Yet other second monomers are quaternary ammonium salts such as, for example, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

In addition to the first monomer of Formula (II) or to a mixture of the first monomer of Formula (II) and one or more of the second monomers described above, the monomer composition can optionally contain a third monomer with at least two polymerizable groups. The polymerizable groups are typically (meth)acryloyl groups. In many embodiments, the third monomer has two or three (meth)acryloyl groups. The third monomer typically is not miscible with the first phase and may or may not be miscible with the first monomer of Formula (II).

Some third monomers have a hydroxyl group. Such monomers can function as crosslinkers like the first monomer of Formula (II) but can provide a polymeric particles with increased hydrophilic character. This can be desirable for the storage and delivery of hydrophilic active agents or for moisture management applications. An example hydroxyl-containing third monomer is glycerol di(meth)acrylate.

Some third monomers are selected to have at least three polymerizable groups. Such third monomers can be added to provide more rigidity to the resulting polymeric particles. The addition of these third monomers tends to minimize swelling of the polymeric particles when exposed to an active agent or when exposed to moisture. Suitable third monomers include, but are not limited to, ethoxylated trimethylolpropane tri(meth)acrylates such as ethoxylated (15) trimethylolpropane triacrylate (commercially available under the trade designation SR9035 from Sartomer) and ethoxylated (20) trimethylolpropane triacrylate (commercially available under the trade designation SR415 from Sartomer); propoxylated trimethylolpropane tri(meth)acrylates such as propoxylated (3) trimethylolpropane triacrylate (commercially available under the trade designation SR492 from Sartomer) and propoxylated (6) trimethylolpropane triacrylate (commercially available under the trade designation CD501 from Sartomer); tris(2-hydroxyethyl) isocyanurate tri(meth)acrylates such as tris(2-hydroxyethyl) isocyanurate triacrylate (commercially available under the trade designations SR368 and SR368D from Sartomer); and propoxylated glyceryl tri(meth)acrylates such as propoxylated (3) glycerol triacrylate (commercially available under the trade designation SR9020 and SR9020HP from Sartomer).

When a third monomer is present in the monomer composition, any suitable amount can be used. The third monomer is often used in an amount up to 20 weight percent based on the total weight of monomers in the monomer composition. In some embodiments, the amount of the third monomer is up to 15 weight percent, up to 10 weight percent, or up to 5 weight percent.

The monomer composition often contains 10 to 100 percent of the first monomer, 0 to 90 weight percent of the second monomer, and 0 to 20 weight percent of the third monomer based on a total weight of monomers in the monomer composition. For example, the monomer composition can contain 10 to 90 weight percent of the first monomer, 10 to 90 weight percent of the second monomer, and 0 to 20 weight percent of the third monomer. The monomer composition can contain 10 to 89 weight percent of the first monomer, 10 to 89 weight percent of the second monomer, and 1 to 20 weight percent of the third monomer based on a total weight of the monomer composition.

In addition to the monomer composition, the second phase contains poly(propylene glycol), which functions as a porogen. The poly(propylene glycol) is soluble in the monomer composition within the second phase but is dispersible within the first phase. Stated differently, the poly(propylene glycol) is completely miscible with the second phase and partially miscible with the first phase. The poly(propylene glycol) is removed after polymerization of the monomer composition to provide pores (e.g., void volumes or free volumes) in the polymeric particle. The poly(propylene glycol) does not have any polymerizable groups (i.e., it is not a monomer) and, in general, is not covalently attached to the polymeric particles that forms within the second phase. It is believed that some of the poly(propylene glycol) become entrained within the polymerized product. The removal of the entrained poly(propylene glycol) results in the formation of hollow polymeric particles. The hollowness of the polymeric particles can be seen in FIG. 2, which is an electron micrograph of a broken polymeric particle. It is further believed that some of the poly(propylene glycol) is positioned on the interface between the first phase and the second phase as the polymerized product is formed in the second phase. The presence of the poly(propylene glycol) at the surface of the forming polymerized product results in the formation of a polymeric particle having surface porosity. The surface porosity can be seen from electron micrographs of the polymeric particles such as in FIG. 1.

Any suitable molecular weight of poly(propylene glycol) can be used as the porogen. The molecular weight can affect the size of the pores that are formed in the polymeric particles. That is, the pore size tends to increase with the molecular weight of the poly(propylene glycol). The weight average molecular weight is often at least 500 grams/mole, at least 800 grams/mole, or at least 1000 grams/mole. The weight average molecular weight of the poly(propylene glycol) can be up to 10,000 gram/mole or greater. For ease of use, a poly(propylene glycol) that is a liquid at room temperature is often selected. Poly(propylene glycol) having a weight average molecular weight up to about 4000 g/mole or 5000 grams/mole tends to be a liquid at room temperature. Poly(propylene glycol) that is not a liquid at room temperature can be used if it is initially dissolved in a suitable organic solvent such as an alcohol (e.g., ethanol, n-propanol, or iso-propanol). The weight average molecular weight of the poly(propylene glycol) is often in a range of 500 to 10,000 grams/mole, in a range of 1000 to 10,000 grams/mole, in a range of 1000 to 8000 grams/mole, in a range of 1000 to 5000 grams/mole, in a range of 1000 to 4000 grams/mole.

The second phase can contain up to 50 weight percent poly(propylene glycol). If higher amounts of the poly(propylene glycol) are used, there may be an insufficient amount of the monomer composition included in the second phase to form polymeric particles that are uniformly shaped. In many embodiments, the second phase can contain up to 45 weight percent, up to 40 weight percent, up to 35 weight percent, up to 30 weight percent, or up to 25 weight percent poly(propylene glycol) based on a total weight of the second phase. The second phase typically contains at least 5 weight percent poly(propylene glycol). If lower amounts of the poly(propylene glycol) are used, the porosity of the resulting polymeric particles may be insufficient. That is, the void volume of the polymeric particles may be insufficient to load and deliver an effective amount of an active agent or to function as a moisture management material. The second phase typically can contain at least 10 weight percent, at least 15 weight percent, or at least 20 weight percent poly(propylene glycol). In some embodiments, the second phase contains 5 to 50 weight percent, 10 to 50 weight percent, 10 to 40 weight percent, 10 to 30 weight percent, 20 to 50 weight percent, 20 to 40 weight percent, or 25 to 35 weight percent poly(propylene glycol) based on the total weight of the second phase.

In some embodiments, the second phase contains 50 to 90 weight percent monomer composition and 10 to 50 weight percent poly(propylene glycol), 60 to 90 weight percent monomer composition and 10 to 40 weight percent poly(propylene glycol), 50 to 80 weight percent monomer composition and 20 to 50 weight percent poly(propylene glycol), or 60 to 80 weight percent monomer composition and 20 to 40 weight percent poly(propylene glycol) based on a total weight of the second phase.

In addition to the monomer composition and poly(propylene glycol), the second phase often contains an initiator for free radical polymerization of the monomer composition. Any suitable initiator known in the art can be used. The initiator can be a thermal initiator, a photoinitiator, or both. The specific initiator used is often selected based on its solubility in the second phase. The initiator is often used at a concentration of 0.1 to 5 weight percent, 0.1 to 3 weight percent, 0.1 to 2 weight percent, or 0.1 to 1 weight percent based on the weight of monomers in the monomer composition.

When a thermal initiator is added to the reaction mixture, polymeric particles can be formed at room temperature (i.e., 20 to 25 degrees Celsius) or at an elevated temperature. The temperature needed for polymerization often depends on the particular thermal initiator used. Examples of thermal initiators include organic peroxides and azo compounds.

When a photoinitiator is added to the reaction mixture, polymeric particles can be formed by the application of actinic radiation. Suitable actinic radiation includes electromagnetic radiation in the infrared region, visible region, ultraviolet region, or a combination thereof.

Examples of photoinitiators suitable in the ultraviolet region include, but are not limited to, benzoin, benzoin alkyl ethers (e.g., benzoin methyl ether and substituted benzoin alkyl ethers such anisoin methyl ether), phenones (e.g., substituted acetophenones such as 2,2-dimethoxy-2-phenylacetophenone and substituted alpha-ketols such as 2-methyl-2-hydroxypropiophenone), phosphine oxides, polymeric photoinitiators, and the like.

Commercially available photoinitiators include, but are not limited to, 2-hydroxy-2-methyl-1-phenyl-propane-1-one (e.g., commercially available under the trade designation DAROCUR 1173 from Ciba Specialty Chemicals), a mixture of 2,4,6-trimethylbenzoyl-diphenyl-phosphine oxide and 2-hydroxy-2-methyl-1-phenyl-propan-1-one (e.g., commercially available under the trade designation DAROCUR 4265 from Ciba Specialty Chemicals), 2,2-dimethoxy-1,2-diphenylethan-1-one (e.g., commercially available under the trade designation IRGACURE 651 from Ciba Specialty Chemicals), a mixture of bis(2,6-dimethoxybenzoyl)-2,4,4-trimethyl-pentylphosphine oxide and 1-hydroxy-cyclohexyl-phenyl-ketone (e.g., commercially available under the trade designation IRGACURE 1800 from Ciba Specialty Chemicals), a mixture of bis(2,6-dimethoxybenzoyl)-2,4,4-trimethyl-pentylphosphine oxide (e.g., commercially available under the trade designation IRGACURE 1700 from Ciba Specialty Chemicals), 2-methyl-1-[4-(methylthio)phenyl]-2-morpholinopropan-1-one (e.g., commercially available under the trade designation IRGACURE 907 from Ciba Specialty Chemicals), 1-hydroxy-cyclohexyl-phenyl-ketone (e.g., commercially available under the trade designation IRGACURE 184 from Ciba Specialty Chemicals), 2-benzyl-2-(dimethylamino)-1-[4-(4-morpholinyl)phenyl]-1-butanone (e.g., commercially available under the trade designation IRGACURE 369 from Ciba Specialty Chemicals), bis(2,4,6-trimethylbenzoyl)-phenylphosphine oxide (e.g., commercially available under the trade designation IRGACURE 819 from Ciba Specialty Chemicals), ethyl 2,4,6-trimethylbenzoyldiphenyl phosphinate (e.g., commercially available from BASF, Charlotte, N.C. under the trade designation LUCIRIN TPO-L), and 2,4,6-trimethylbenzoyldiphenylphosphine oxide (e.g., commercially available from BASF, Charlotte, N.C. under the trade designation LUCIRIN TPO).

The reaction mixture often includes at least 5 weight percent of the second phase (dispersed phase) and up to 95 weight percent of the first phase (continuous phase). In some embodiments, the reaction mixture contains 5 to 40 weight percent second phase and 60 to 95 weight percent first phase, 5 to 30 weight percent second phase and 70 to 95 weight percent first phase, 10 to 30 weight percent second phase and 70 to 90 weight percent first phase, or 5 to 20 weight percent second phase and 80 to 95 weight percent first phase. The weight percents are based on a total weight of the reaction mixture.

To prepare the polymeric particles or beads, droplets of the second phase are formed in the first phase. The components of the second phase are often mixed together prior to addition to the first phase. For example, the monomer composition, initiator, and the poly(propylene glycol) can be blended together and then this blended composition, which is the second phase, can be added to the first phase. The resulting reaction mixture is often mixed under high shear to form a micro-emulsion. The size of the dispersed second phase droplets can be controlled by the amount of shear or the mixing rate. The size of the droplets can be determined by placing a sample of the mixture under an optical microscope prior to polymerization. Although any desired droplet size can be used, the average droplet diameter is often less than 200 micrometers, less than 100 micrometers, less than 50 micrometers, less than 25 micrometers, less than 10 micrometers, or less than 5 micrometers. For example, the average droplet diameter can be in the range of 1 to 200 micrometers, 1 to 100 micrometers, 5 to 100 micrometers, 5 to 50 micrometers, 5 to 25 micrometers, or 5 to 10 micrometers.

If a photoinitiator is used, the reaction mixture is often spread on a non-reactive surface to a thickness that can be penetrated by the desired actinic radiation. The reaction mixture is spread using methods that do not cause the droplets to coalesce. For example, the reaction mixture can be formed using an extrusion method. Often, the actinic radiation is in the ultraviolet region of the electromagnetic spectrum. If the ultraviolet radiation is applied from only the top surface of the reaction mixture layer, the thickness of the layer can be up to about 10 millimeters. If the reaction mixture layer is exposed to ultraviolet radiation from both the top and bottom surfaces, the thickness can be greater such as up to about 20 millimeters. The reaction mixture is subjected to the actinic radiation for a time sufficient to react the monomer composition and form polymeric particles. The reaction mixture layer is often polymerized within 5 minutes, within 10 minutes, within 20 minutes, within 30 minutes, within 45 minutes, or within 1 hour depending on the intensity of the actinic radiation source and the thickness of the reaction mixture layer.

If a thermal initiator is used, the droplets can be polymerized while continuing to mix the reaction mixture. Alternatively, the reaction mixture can be spread on a non-reactive surface to any desired thickness. The reaction mixture layer can be heated from the top surface, from the bottom surface, or both to form the polymeric particles. The thickness is often selected to be comparable to that use with the use of actinic radiation such as ultraviolet radiation.

In many embodiments, a photoinitiator is preferred over a thermal initiator because lower temperatures can be used for polymerization. That is, the use of actinic radiation such as ultraviolet radiation can be used to minimize degradation of various components of the reaction mixture that might be sensitive to temperatures needed for use with thermal initiators. Further, the temperatures typically associated with the use of thermal initiators may undesirably alter the solubility of the various components of the reaction mixture between the first phase and the dispersed second phase.

During the polymerization reaction, the monomer composition reacts within the dispersed second phase droplets suspended in the first phase. As the polymerization progresses, the poly(propylene glycol) included in the second phase gets partially entrained within the polymerized product. Although it is possible that some portion of the poly(propylene glycol) can be covalently attached to the polymeric product through a chain transfer reaction, preferably the poly(propylene glycol) is not bonded to the polymeric product. The polymerized product is in the form of particles. In some embodiments, the particles are polymeric beads having a relatively uniform size and shape.

After formation of the polymerized product (i.e., polymeric particles containing entrained poly(propylene glycol)), the polymerized product can be separated from the first phase. Any suitable separation method can be used. For example, water is often added to lower the viscosity of the first phase. The particle so the polymerized product can be separated by decantation, filtration, or centrifugation. The particles of the polymerized product can be further washed by suspending them in water and collecting them a second time by decantation, filtration, centrifugation, or drying.

The particles of the polymerized product can then be subjected to one or more washing steps to remove the poly (propylene glycol) porogen. Suitable solvents for removing the poly(propylene glycol) include, for example, acetone, methyl ethyl ketone, toluene, and alcohols such as ethanol, n-propanol, or iso-propanol. Stated differently, the entrained poly(propylene glycol) is removed from the polymerized product using solvent extraction methods. Pores are created where the poly(propylene glycol) previously resided.

In many embodiments, the resulting porous polymeric particles (the polymerized product after removal of the poly (propylene glycol) porogen) have an average diameter that is less than 200 micrometers, less than 100 micrometers, less than 50 micrometers, less than 25 micrometers, less than 10 micrometers, or less than 5 micrometers. For example, the porous polymeric particles can have an average diameter in the range of 1 to 200 micrometers, 1 to 100 micrometers, 5 to 100 micrometers, 5 to 50 micrometers, 5 to 25 micrometers, or 5 to 10 micrometers.

The polymeric particles usually have multiple pores distributed over the surface of the particles. In some embodiments, the polymeric particles are hollow in addition to having multiple pores distributed over the surface of the particles. As used herein, the term "hollow" refers to polymeric particles that have a polymeric outer shell surrounding an inner region (cavity or core) that is not polymeric. The presence of the hollow interior can be seen in scanning electron micrographs of broken polymeric particles as shown, for example, in FIG. 2. After removal of the poly(propylene glycol) porogen, the resulting polymeric particles tend to be more porous than polymeric particles prepared using a first phase that is predominately water such as a first phase containing a polysaccharide dissolved in water.

Based on the diameter of the particles and the dimensions of the pores, the polymeric particles often can be described as being micro-particles (the average diameter is typically in a range of 1 to 200 micrometers, in the range of 1 to 100 micrometers, or in the range of 1 to 50 micrometers) and nano-porous (the pores have dimensions in an nanometer range such as in the range of 1 to 200 nanometers, in the range of 10 to 200 nanometers, in the range of 20 to 200 nanometers, or in the range of 50 to 200 nanometers). In The porous polymeric particles or the hollow and porous polymeric particles are well suited for storage and delivery of an active agent. That is, in certain embodiments, the porous polymeric particles further include an active agent. In particular, if all of the monomers in the monomer composition are hydrophobic, the polymeric particles tend to be hydrophobic (i.e., hydrophobic polymeric particles) and can accept (e.g., be loaded with) hydrophobic active agents. If some of the monomers in the monomer composition are hydrophilic, however, the polymeric particles tend to have sufficient hydrophilic character (i.e., hydrophilic polymeric particles) to accept hydrophilic active agents. Further, if the monomer composition includes a mixture of both hydrophobic monomers and hydrophilic monomers, the polymeric particles tend to have sufficient hydrophobic and hydrophilic character to accept both hydrophobic and hydrophilic active agents. In some embodiments, polymeric particles having both hydrophobic and hydrophilic character can be desirable.

Some active agents of particular interest are biologically active agents. As used herein, the term "biologically active agent" refers to a compound that has some known effect on living systems such as, for example, a bacteria or other microorganism, plant, fish, insect, or mammal. The bioactive agent is added for the purpose of affecting the living system such as affecting the metabolism of the living system. Examples of biologically active agents include, but are not limited to, medicaments, herbicides, insecticides, antimicrobial agents, disinfectants and antiseptic agents, local anesthetics, astringents, antifungal agents (i.e., fungicides), antibacterial agents, growth factors, herbal extracts, antioxidants, steroids or other anti-inflammatory agents, compounds that promote wound healing, vasodilators, exfoliants, enzymes, proteins, carbohydrates, silver salts, and the like. Still other bioactive agents include artificial tanning agents, tanning accelerants, skin smoothing agents, skin tightening agents, anti-wrinkle agents, skin repair agents, anti-itch agents, hair growth agents, anti-acne agents, hair removal agents, corn removal agents, callus removal agents, wart removal agents, sunscreen agents, insect repellant agents, deodorants and antiperspirant agents, hair colorants or bleaching agents, and anti-dandruff agents. Any other suitable biologically active agent known in the art can be used. In some particular embodiments, the active agent are herbicides, insecticides, or fungicides.

Any suitable method can be used to load (i.e., to position) the active agent into the porous polymeric particle once the porogen has been removed. In some embodiments, the active agent is a liquid and the polymeric particles are mixed with the liquid to load the active agent. In other embodiments, the active agent can be dissolved in a suitable organic solvent or water and the polymeric particles are exposed to the resulting solution. Any organic solvent that is used is typically selected so that it does not dissolve the polymeric particles. When an organic solvent or water is used, at least some of the organic solvent or water may be loaded by the polymeric particle in addition to the active agent.

When the active agent is dissolved in an organic solvent or water, the concentration is typically selected to be as great as possible to shorten the time needed for loading of a suitable amount of the active agent onto the polymeric particle. The amount of active agent loaded and the amount of time required for loading are often dependent, for example, on the composition of the monomers used to form the polymeric particle, the rigidity of the polymeric particle (e.g., the amount of crosslinking), and the compatibility of the active agent with the polymeric particle. The loading time is often less than 24 hours, less than 18 hours, less than 12 hours, less than 8 hours, less than 4 hours, less than 2 hours, less than 1 hour, less than 30 minutes, less than 15 minutes, or less than 5 minutes. After loading, the particles are typically separated from the solution containing the active agent by decantation, filtration, centrifugation, or drying.

The volume of active agent loaded can be up to the volume of poly(propylene glycol) removed from the polymerized product used to form the polymeric particles. That is, the active agent can fill the voids left after removal of the poly (propylene glycol). In many embodiments, the amount of active agent loaded can be up to 50 weight percent based on a total weight of the polymeric particle after loading (i.e., polymeric particles plus the loaded active agent). In some example loaded polymeric particles loaded, the amount of the active agent can be up to 40 weight percent, up to 30 weight percent, 25 weight percent, up to 20 weight percent, up to 15 weight percent, up to 10 weight percent, or up to 5 weight percent. The amount of active agent is typically at least 0.1 weight percent, at least 0.2 weight percent, at least 0.5 weight percent, at least 1 weight percent, at least 5 weight percent, or at least 10 weight percent. Some loaded polymeric particles contain 0.1 to 50 weight percent, 0.5 to 50 weight percent, 1 to 50 weight percent, 5 to 50 weight percent, 1 to 40 weight percent, 5 to 40 weight percent, 10 to 40 weight percent, or 20 to 40 weight percent active agent. Because the porous polymeric particles tend to be highly crosslinked, they tend to swell little even after loading of the active agent. That is, the average sizes of the porous polymeric particles are comparable before and after loading of the active agent.

The active agent is not covalently bonded to the polymeric particles. Under suitable diffusion controlled conditions, the active agent can be released (i.e., delivered) from the polymeric particles. The release can be complete or nearly complete (e.g., greater than 90 percent, greater than 95 percent, greater than 98 percent, greater than 99 percent complete).

In some embodiments, the polymeric particles with loaded active agent that are hydrophobic can be suspended in water. The active agent is often not extracted from the polymeric particles into the water. The suspension can be in the form of a lotion. The suspension (e.g., lotion) can contain up to 50 weight percent polymeric particles with loaded active agent. For example, the suspension can contain up to 40 weight percent, up to 30 weight percent, up to 25 weight percent, up to 20 weight percent, or up to 10 weight percent polymeric particles with loaded active agent.

In other embodiments, the polymeric particles that are prepared using a second monomer or third monomer that is hydrophilic can be used as a moisture management material. That is, these hydrophilic polymeric particles can be used to control moisture (e.g., to adsorb moisture). As used herein, the term "moisture" refers to water or to a water-containing solution. Applications include, but are not limited to, adsorption of wound fluids in wound dressing articles, adsorption of sweat in sweat management articles, and adsorption of urine in incontinence management articles. The hydrophilic polymeric particles can be used to both manage moisture and to deliver a hydrophilic active agent. For example, hydrophilic polymeric particles can be used in a wound dressing to both manage water and to deliver a hydrophilic antimicrobial agent.

The polymeric particles are not tacky. This makes them well suited for applications where the particles are included in a layer of an article that is positioned adjacent to skin. Additionally, because the polymeric particles tend to be highly crosslinked, they tend to swell little even when an active agent is loaded or moisture is adsorbed. That is, the polymeric particles undergo a relatively small change in volume when an active agent is loaded or moisture is adsorbed.

In some applications, the polymeric particles are combined with a polymeric binder to prepare a coating composition. The coating composition can then be applied to any suitable substrate surface. Suitable binders include, for example, polyurethanes, polyacrylates, poly(ethylene glycols), polyesters, poly(lactic acid), alginic acid, cellulose or cellulose derivatives, and the like. The binders can be linear or can be crosslinked. It is often preferable to use binders that can chemically react with groups present in the polymeric particles such as hydroxyl groups. For example, a binder can have functional groups such as silyl groups or carboxyl groups. Many of the above listed binders have suitable functional groups or can be modified to include such functional groups. For example, polyurethanes can be provided with silyl groups.

The term "silyl" refers to a monovalent group of formula —Si(R)$_3$ where R is hydroxyl, a hydrolyzable group, or a non-hydrolyzable group. In many embodiments, the silyl group is a "reactive silyl" group, which means that the silyl group contains at least one R group that is a hydroxyl group or hydrolyzable group. Some reactive silyl groups are of formula —Si(R$^a$)$_{3-x}$(R$^b$)$_x$ where each group R$^a$ is independently hydroxyl or a hydrolyzable group and each group R$^b$ is independently a non-hydrolyzable group. The variable x is an integer equal to 0, 1, or 2. The term "hydrolyzable group" refers to a group that can react with water having a pH of 1 to 10 under conditions of atmospheric pressure. The hydrolyzable group is often converted to a hydroxyl group when it reacts. The hydroxyl group often undergoes further reactions. Typical hydrolyzable groups include, but are not limited to, alkoxy (e.g., alkoxy groups with 1 to 10 carbon atoms), aryloxy (e.g., an aryloxy with 6 to 10 carbon atoms), aralkyloxy (e.g., an aralkyloxy with 6 to 12 carbon atoms), acyloxy (e.g., an acyloxy with 2 to 10 carbon atoms), or halo (e.g., chloro, bromo, or iodo). As used herein, the term is often used in reference to one of more groups bonded to a silicon atom in a silyl group. The term "non-hydrolyzable group" refers to a group that cannot react with water having a pH of 1 to 10 under conditions of atmospheric pressure. Typical non-hydrolyzable groups include, but are not limited to alkyl (e.g., an alkyl with 1 to 10 carbon atoms), aryl (e.g., an aryl with 6 to 10 carbon atoms), and aralkyl (e.g., an aralkyl with 6 to 12 carbon atoms). As used herein, the term is often used in reference to one of more groups bonded to a silicon atom in a silyl group.

In some embodiments, the binder is a polyurethane. Polyurethanes tend to have good adhesion to the polymeric particles. In some embodiments, the polyurethane has terminal silyl groups that can react with polymeric particles having hydroxyl groups (i.e., polymeric particles prepared from a monomer composition containing a second monomer with a hydroxy group, a third monomer with a hydroxyl group, or both). Such binders are described, for example, in U.S. Pat. No. 5,554,686 (Frisch, Jr. et al.).

Typically, the coating compositions contain up to 85 percent or more of the polymeric particles. For example, the coating composition can contain up to 80 weight percent, up to 70 weight percent, or up to 60 weight percent polymeric particles. The coating compositions typically contain at least 10 weight percent, at least 20 weight percent, at least 30 weight percent, or at least 40 weight percent polymeric particles. In some embodiments, the coatings contain 20 to 85 weight percent, 40 to 85 weight percent, 50 to 85 weight percent, or 60 to 85 weight percent of the polymeric particles based on a total weight of the coating composition. Adding more polymeric particles tends to increase the amount of active agent that can be stored and/or delivered or the amount of moisture that can be adsorbed.

The amount of binder in the coating composition is often selected to be an amount sufficient to form a coating layer but not enough to cover all of the pores on the surface of the polymeric particles. In some embodiments, the coating compositions contain 15 to 50 weight percent binder and 50 to 85 weight percent polymeric particles based on a total weight of solids in the coating compositions. For example, the coating compositions can contain 15 to 45 weight percent binder and 55 to 85 weight percent polymeric particles, 20 to 45 weight percent binder and 55 to 80 weight percent polymeric particles, or 25 to 40 weight percent binder and 60 to 75 weight percent polymeric particles.

The coating composition can be applied to any suitable substrate. In some embodiments, the substrate is porous. For example, the substrate can be fibrous and the fibrous substrate can be woven or non-woven. The polymeric particles can be distributed on a surface of the fibrous substrate, distributed throughout the fibrous substrate, or both. The fibers used in the fibrous substrate can be constructed of any suitable material and is often a combination of one of more materials. In some embodiments, at least one of the fibers used in the fibrous substrate has groups that can interact with a polymeric binder that is used in a coating composition that contains the polymeric particles.

In one particular example, the polymeric particles are combined with a polyurethane binder having silyl groups to form a coating composition. The coating composition is applied to a fibrous substrate having hydroxyl groups. For example, the substrate can contain cellulose fibers. One such fibrous substrate that contains fibers of both polypropylene and cellulose is commercially available under the trade designation FPN336 from Fiberweb Corporation, Old Hickory, Tenn., USA. Alternatively, the hydroxyl groups on a surface of a substrate can be generated by corona treatment of a substrate that does not contain such groups.

Various embodiments are provided that are reaction mixtures, porous polymeric particles, methods of making porous polymeric particles, or articles containing the porous polymeric particles.

Embodiment 1 is a reaction mixture that includes (a) a first phase and (b) a second phase dispersed in the first phase, wherein a volume of the first phase is greater than a volume of the second phase. The first phase contains (i) a compound of Formula (I)

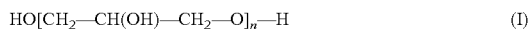
$$HO[CH_2—CH(OH)—CH_2—O]_n—H \qquad (I)$$

where the variable n is an integer equal to at least 1 and (ii) a nonionic surfactant. The second phase contains (i) a monomer composition comprising a monomer of Formula (II)

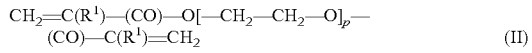
$$CH_2=C(R^1)—(CO)—O[—CH_2—CH_2—O]_p—$$
$$(CO)—C(R^1)=CH_2 \qquad (II)$$

where the variable p is an integer equal to at least 1 and where $R^1$ is hydrogen or methyl, and (ii) a poly(propylene glycol) having a weight average molecular weight of at least 500 grams/mole.

Embodiment 2 is the reaction mixture of embodiment 1, wherein the monomer composition further comprises at least one second monomer having one (meth)acryloyl group.

Embodiment 3 is the reaction mixture of embodiment 2, wherein the second monomer comprises a hydroxyl-containing monomer.

Embodiment 4 is the reaction mixture of embodiment 2, wherein the second monomer comprises a sulfonyl-containing monomer.

Embodiment 5 is the reaction mixture of embodiment 2, wherein the second monomer comprises a hydroxyl-containing monomer and a sulfonyl-containing monomer.

Embodiment 6 is the reaction mixture of any one of embodiments 2 to 5, wherein the second monomer is of Formula (III).

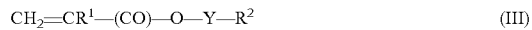
$$CH_2=CR^1—(CO)—O—Y—R^2 \qquad (III)$$

In Formula (III), group $R^1$ is hydrogen or methyl. Group Y is a single bond, alkylene, oxyalkylene, or poly(oxyalkylene). Group $R^2$ is a carbocyclic group or heterocyclic group.

Embodiment 7 is the reaction mixture of any one of embodiments 1 to 6, wherein a volume ratio of the first phase to the second phase is at least 2:1.

Embodiment 8 is the reaction mixture of any one of embodiment 1 to 7, wherein the variable n in the compound of Formula (I) is equal to 1.

Embodiment 9 is the reaction mixture of any one of embodiments 1 to 8, wherein the nonionic surfactant is present in an amount in a range of 0.5 to 15 weight percent based on a total weight of the first phase.

Embodiment 10 is the reaction mixture of any one of embodiment 1 to 9, wherein the first monomer of Formula (I) is a polyethylene glycol di(meth)acrylate.

Embodiment 11 is a porous polymeric particle that is formed from a polymerized product of a reaction mixture. The reaction mixture includes (a) a first phase and (b) a second phase dispersed in the first phase, wherein a volume of the first phase is greater than a volume of the second phase. The first phase contains (i) a compound of Formula (I)

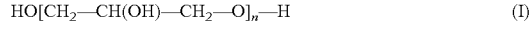
$$HO[CH_2—CH(OH)—CH_2—O]_n—H \qquad (I)$$

where the variable n is an integer equal to at least 1 and (ii) a nonionic surfactant. The second phase contains (i) a monomer composition comprising a monomer of Formula (II)

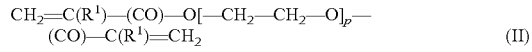
$$CH_2=C(R^1)—(CO)—O[—CH_2—CH_2—O]_p—$$
$$(CO)—C(R^1)=CH_2 \qquad (II)$$

where the variable p is an integer equal to at least 1 and where $R^1$ is hydrogen or methyl, and (ii) a poly(propylene glycol) having a weight average molecular weight of at least 500 grams/mole. The poly(propylene glycol) is removed from the polymerized product to provide the porous polymeric particle.

Embodiment 12 is the porous polymeric particle of embodiment 11, wherein the porous polymeric particle is in a form of hollow beads.

Embodiment 13 is the porous polymeric particle of embodiment 11 or 12, wherein the monomer composition further comprises a second monomer having one (meth)acryloyl group.

Embodiment 14 is the porous polymeric particle of embodiment 13, wherein the monomer second monomer comprises a hydroxyl-containing monomer, a sulfonyl-containing monomer, or both.

Embodiment 15 is the porous polymeric particle of any one of embodiments 11 to 14, wherein an active agent is loaded or moisture is adsorbed within at least some of the pores of the porous polymeric particle.

Embodiment 16 is the porous polymeric particle of embodiment 13, wherein the second monomer is of Formula (III).

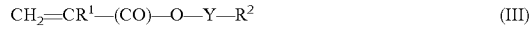
$$CH_2=CR^1—(CO)—O—Y—R^2 \qquad (III)$$

In Formula (III), group $R^1$ is hydrogen or methyl. Group Y is a single bond, alkylene, oxyalkylene, or poly(oxyalkylene). Group $R^2$ is a carbocyclic group or heterocyclic group.

Embodiment 17 is the porous polymeric particle of any one of embodiments 11 to 16, wherein a volume ratio of the first phase to the second phase is at least 2:1.

Embodiment 18 is the porous polymeric particle of any one of embodiment 11 to 17, wherein the variable n in the compound of Formula (I) is equal to 1.

Embodiment 19 is the porous polymeric particle of any one of embodiments 11 to 18, wherein the nonionic surfactant is present in an amount in a range of 0.5 to 15 weight percent based on a total weight of the first phase.

Embodiment 20 is the porous polymeric particle of any one of embodiment 11 to 19, wherein the first monomer of Formula (I) is a polyethylene glycol di(meth)acrylate.

Embodiment 21 is an article is that contains 1) a substrate and 2) porous polymeric particles distributed on a surface of the substrate, throughout the substrate, or a combination thereof. The porous polymeric particles contain a polymerized product of a reaction mixture that includes (a) a first phase and (b) a second phase dispersed in the first phase, wherein a volume of the first phase is greater than a volume of the second phase. The first phase contains (i) a compound of Formula (I)

$$HO[CH_2-CH(OH)-CH_2-O]_n-H \quad (I)$$

where the variable n is an integer equal to at least 1 and (ii) a nonionic surfactant. The second phase contains (i) a monomer composition comprising a monomer of Formula (II)

$$CH_2=C(R^1)-(CO)-O[-CH_2-CH_2-O]_p-(CO)-C(R^1)=CH_2 \quad (II)$$

where the variable p is an integer equal to at least 1 and where $R^1$ is hydrogen or alkyl, and (ii) a poly(propylene glycol) having a weight average molecular weight of at least 500 grams/mole. The poly(propylene glycol) is removed from the polymerized product to provide the porous polymeric particles.

Embodiment 22 is the article of embodiment 21, wherein the substrate is porous.

Embodiment 23 is the article of embodiment 21 or 22, wherein article comprises the substrate and a coating layer attached to the substrate, wherein the coating layer comprises a binder and the porous polymeric particles.

Embodiment 24 is the article of embodiment 23, wherein the porous polymeric particles have hydroxyl groups and wherein the binder has group reactive with the hydroxyl groups.

Embodiment 25 is the article of embodiment 24, wherein the binder is a polyurethane with silyl groups that react with the hydroxyl groups of the porous polymeric particles.

Embodiment 26 is the article of any one of embodiments 21 to 25, wherein the substrate is a woven or non-woven fibrous substrate.

Embodiment 27 is the article of embodiment 23, wherein the substrate has hydroxyl groups and the coating composition comprises a binder having functional groups that react with the hydroxyl groups of the substrate.

Embodiment 28 is the article of any one of embodiments 21 to 27, wherein an active agent is loaded or moisture is adsorbed within at least some of the pores of the porous polymeric particles.

Embodiment 29 is a method of making a porous polymeric particle. The method includes preparing a first phase that contains (i) a compound of Formula (I)

$$HO(-CH_2-CH(OH)-CH_2-O)_n-H \quad (I)$$

where the variable n is an integer equal to at least 1 and (ii) a nonionic surfactant. The method further includes forming a second phase, wherein a volume of the first phase is greater than a volume of the second phase. The second phase contains (i) a monomer composition comprising a monomer of Formula (II)

$$CH_2=C(R^1)-(CO)-O[-CH_2-CH_2-O]_p-(CO)-C(R^1)=CH_2 \quad (II)$$

where the variable p is an integer equal to at least 1 and where $R^1$ is hydrogen or alkyl, and (ii) a poly(propylene glycol) having a weight average molecular weight of at least 500 grams/mole. The method still further includes providing a reaction mixture by dispersing the second phase in the first phase, curing the monomer composition within the reaction mixture to form a polymerized product, and then removing the poly(propylene glycol) from the polymerized product to form the porous polymer particle.

Embodiment 30 is the method of embodiment 29, wherein a volume ratio of the first phase to the second phase is at least 2:1.

Embodiment 31 is the method of embodiment 29 or 30, wherein the porous polymeric particle is in a form of a hollow bead.

Embodiment 32 is the method of any one of embodiments 29 to 31, wherein the method further comprises loading an active agent.

Embodiment 33 is the method of embodiment 32, wherein the active agent is hydrophobic.

Embodiment 34 is the method of embodiment 32, wherein the active agent is hydrophilic and the monomer composition comprises a second monomer that is a hydroxyl-containing monomer, a sulfonyl-containing monomer, or both.

Embodiment 35 is a porous polymeric particle comprising a polymerized product of a monomer composition comprising a monomer of Formula (II)

$$CH_2=C(R^1)-(CO)-O[-CH_2-CH_2-O]_p-(CO)-C(R^1)=CH_2 \quad (II)$$

where the variable p is an integer equal to at least 1 and where $R^1$ is hydrogen or alkyl. The polymeric particle has pores that contains poly(propylene glycol) or an active agent.

Embodiment 36 is an article comprising 1) a substrate and 2) porous polymeric particles distributed on a surface of the substrate, throughout the substrate, or a combination thereof. The porous polymeric particles comprise a polymerized product of a monomer composition comprising a monomer of Formula (II)

$$CH_2=C(R^1)-(CO)-O[-CH_2-CH_2-O]_p-(CO)-C(R^1)=CH_2 \quad (II)$$

where the variable p is an integer equal to at least 1 and where $R^1$ is hydrogen or alkyl. The polymeric particles have pores that contains poly(propylene glycol) or an active agent.

EXAMPLES

Materials

Ethylene diamine, and lecithin were obtained from Alfa Aesar Corporation, Ward Hill, Mass., USA.

Letheen neutralizing broth, tryptic soy broth, and agar were obtained from Becton Dickinson & Company, Franklin Lakes, N.J., USA.

Dibutyltin dilaurate and (hydroxypropyl)methyl cellulose were obtained from Sigma Aldrich, St. Louis, Mo., USA.

Methyl ethyl ketone (MEK) was obtained from Avantor Performance Materials, Center Valley, Pa., USA.

Triethylamine was obtained from EMD Millipore Chemicals Corporation, Billerica, Mass., USA.

Glycerol di(meth)acrylate was obtained from TCI America Corporation, Portland, Oreg., USA.

2-Sulfoethyl methacrylate was obtained from Polysciences Incorporated, Warrington, Pa., USA.

SR339 is a trade designation for 2-phenoxyethyl acrylate obtained from Sartomer Corporation, Exton, Pa., USA.

SR603OP is a trade designation for polyethylene glycol (average molecular weight of 400 grams/mole) dimethacrylate obtained from Sartomer Corporation, Exton, Pa., USA.

3-Acrylamidopropyl)trimethyl ammonium chloride was obtained as a 75 weight percent solution in water from Sigma Aldrich, Saint Louis, Mo., USA.

2-Carboxyethyl acrylate can be obtained from Sigma Aldrich, Saint Louis, Mo., USA 2-Hydroxyethyl methacrylate can be obtained from Sigma Aldrich, Saint Louis, Mo., USA PPG refers to polypropylene glycol (average molecular weight of 4000 grams/mole) obtained from Polysciences Incorporated, Warrington, Pa., USA.

IRGACURE 819 is a trade designation for bis(2,4,6-trimethylbenzoyl)-phenylphospineoxide obtained from BASF Corporation, Florham Park, N.J., USA. This was used as a photoinitiator.

APG 325 is a trade designation for a blend of decyl and undecyl glucosides, obtained from BASF Corporation, Florham Park, N.J., USA. This was used as a surfactant.

POLYOL C-2090 is a trade designation for a mixture of 3-methyl-1,5-pentanediol and 1,6-hexanediol obtained from Kuraray Corporation Ltd, Japan. The ratio of the moles of the two components in the mixture is 9:1.

DESMODUR I is a trade designation for isophorone diisocyanate obtained from Bayer Corporation, Pittsburgh, Pa., USA.

DMPA refers to dimethylol propionic acid obtained from TCI America Corporation, Portland, Oreg., USA.

1,4-butendiol (1,4-BDO) was obtained from Avantor Performance Materials, Center Valley, Pa., USA under trade designation "J. T. Baker 1,4-BDO".

DYNASYLAN AMEO is a trade designation for 3-aminopropyltriethoxysilane obtained from Evonik Industries AG, Essen, Germany Polyaminopropyl biguanide (PHMB), a 20% (weight/volume) solution in water that is commercially available under the trade designation "COSMOCIL CQ" from Lonza Group Limited, Basel, Switzerland.

Example 1

50 grams of SR339 and 50 grams of SR603OP were mixed with 43 grams of PPG and 250 milligrams of IRGACURE 819. The mixture was stirred vigorously for 20 minutes while heating from 40 to 50° C. This second phase mixture was then added to a first phase that contained 750 grams of glycerol that had previously been mixed with 7.5 grams of APG 325. The mixture was then shear mixed for 20 minutes using a shear mixer at 700 rpm, spread between two sheets of a polyethylene terephthalate (PET) film, and cured for 15 to 20 minutes with a 100 Watt, long-wavelength BLACK RAY UV lamp (obtained from UVP, LLC of Upland, Calif., USA) positioned approximately 15 centimeters above the material.

The cured mixture was then dispersed in 500 milliliters of water, shaken vigorously for 30 minutes, and centrifuged at 3000 rpm in an EPPENDORF 5810 R centrifuge (obtained from Eppendorf International, Hauppauge, N.Y., USA) for 30 minutes. The supernatant was removed and the resulting particles were re-suspended in 500 milliliters of water and subsequently centrifuged again. The supernatant was then removed and the particles were suspended in 500 milliliters of isopropyl alcohol and shaken for 20 minutes. The mixture was centrifuged again to isolate the particles and the supernatant was discarded.

A scanning electron micrograph (SEM) of an Example 1 particle is shown in FIG. 1. The SEM was generated using a Hitachi Model S-4700 Field Emission Scanning Electron Microscope (obtained from Hitachi High-Technologies America, Inc., Schaumburg, Ill., USA).

Another SEM of the Example 1 particles is shown in FIG. 2. One of the particles was broken and the free space inside the particle is visible. That is, the particle is hollow. This SEM was generated using a JEOL JCM-5000 Scanning Electron Micrograph obtained from JEOL USA, Incorporated, Peabody, Mass., USA.

Comparative Example A 50 grams of SR339 and 50 grams of SR603OP were mixed with 43 grams of PPG and 250 milligrams of IRGACURE 819. The mixture was stirred vigorously for 20 minutes while heating to 40 to 50° C. This mixture was then added to 750 grams of a solution of 20% (weight/weight) (hydroxypropyl) methyl cellulose in water that had previously been mixed with 7.5 grams of APG 325. The mixture was shear mixed, spread between two sheets of PET film, and cured with an ultraviolet lamp as described in Example 1. The particles were washed and isolated exactly as described in Example 1.

The SEM of Comparative Example A is shown in FIG. 3. This SEM was generated using a JEOL JCM-5000 Scanning Electron Micrograph obtained from JEOL USA, Incorporated, Peabody, Mass., USA.

Porosity and Surface Area Measurements

The porosity and surface area of Comparative Example A and Example 1 particles were measured using a model TRISTAR 3000 surface area and porosity analyzer commercially available from Micromeritics Inc., Norcross, Ga., USA. Approximately 0.1-1.0 grams each of Comparative Example A and Example 1 particles were transferred to a 1.3 centimeters (0.5 inch) diameter sample tube and degassed using a system commercially available from Micromeritics Inc., under the trade designation VACPREP 061 for 24 hours at 110° C. under vacuum below 0.015 mbar (1.5 Pa). After degassing, the samples were allowed to cool for 10 minutes under vacuum at ambient temperature (i.e., 20 to 25° C.), and then loaded onto a TRISTAR 3000 surface area and porosity analyzer.

A 45 point adsorption/40 point desorption isotherm was set up with relative pressures ($P/P_o$) starting at about 0.0 up to about 1.0 with a tighter distribution of points between 0.95 and 1.0. No first "pressure fixed dose" was set. The maximum volume increment was set at 10.00 cc/gram at STP, the "absolute pressure tolerance" was set at 5 mm Hg (0.67 kPa), and the "relative pressure tolerance" was set at 2.0%, "Fast evacuation" and "leak test" options were not used. With the Dewar of liquid nitrogen lowered (i.e., the sample was not in the liquid nitrogen), an evacuation time of 0.5 hours was implemented during the free space measurement. The Dewar was raised for analysis (i.e., the tube containing the sample was placed in liquid nitrogen). At 77.350° K (the temperature of liquid nitrogen), $P_o$ was measured at 120-minute intervals during the analysis. The gas adsorptive properties using a standard $P_{stat}$ versus temperature table for nitrogen gas were set at the following values: non-ideality factor, 0.0000620; density conversion factor, 0.0015468; molecular cross-sectional area, 0.162 nm$^2$. BJH (a description of BJH theory can be found in E. P. Barrett, L. S. Joyner, and P. P. Halenda, *J. Am.*

*Chem. Soc.*, 73, 373 (1951)) desorption cumulative pore volumes and cumulative surface areas were calculated for pores between 17 angstroms and 2,000 angstroms diameter (corresponding to pores between 2 and 200 nanometers), and based on quantity of nitrogen adsorbed at each relative pressure during the 45 adsorption points and 40 desorption points. Results are shown in table 1.

TABLE 1

Characterization of Porosity

| Polymeric Particles | BJH desorption cumulative surface area of material (m²/gram) | BJH desorption cumulative volume of pores (cc/gram) |
|---|---|---|
| Comparative Example A | 1.045 | 0.044 |
| Example 1 | 4.118 | 0.149 |

Example 2

The Example 2 polymeric particles were synthesized as described in Example 1 except that the second phase contained 100 grams of SR 603OP, 43 grams of PPG, and 250 milligrams of IRGACURE 819. The monomer SR 339 was not used.

Example 3

Example 3 was run in the same manner as Example 1 except that the second phase contained 50 grams of SR339, 50 grams of SR603OP, and 5 grams 2-sulfoethyl methacrylate that were mixed with 43 grams of PPG and 250 milligrams of IRGACURE 819

Example 4

Example 4 was run in the same manner as Example 2 except that the second phase contained 100 grams of SR 603OP, 5 grams 2-sulfoethyl methacrylate, and 5 grams of glycerol dimethacrylate that were mixed with 43 grams of PPG and 250 milligrams of IRGACURE 819.

Example 5

A silane-terminated waterborne polyurethane dispersion was prepared as follows. 70.76 grams POLYOL C-2090 and 24.23 grams DESMODUR I were added to a 500-milliliter four-necked round-bottom flask equipped with a mechanical stirrer, thermometer, condenser, and nitrogen inlet. The polyaddition reaction was carried out while stirring at 78° C. in the presence of 0.01 percent dibutyltin dilaurate (weight/weight based on weight of the total solids in the flask). After 1 hour, 5.0 grams DMPA and 20 grams MEK were added and the reaction was carried out for an additional 2 hours until DMPA was dissolved. Then, the NCO terminated-prepolymer was chain extended by adding 1.31 grams of 1,4-BDO, and allowed to react for 1.5 hours. The resulting prepolymers were cooled to 40° C. and neutralized for 30 minutes by the addition of 3.78 grams of triethylamine under stirring, and then partially terminated by the addition of 6.375 g DYNASYLAN AMEO. An aqueous dispersion was made by slowly adding water to silane-terminated polyurethane prepolymers with vigorous stirring. Once the prepolymer was dispersed, 1.09 grams of ethylene diamine dissolved in 5.0 grams of water was slowly added for further chain extension. MEK was removed at 40° C. on a rotary evaporator, resulting in a silane-terminated polyurethane dispersion with a solid content of 50 percent by weight.

10 grams of particles from Example 3 were added to 5 grams of the dispersion of silane terminated polyurethane and 4 grams of water. The mixture was stirred for 15 minutes before coating on FPN336 polypropylene and cellulose nonwoven material (31 grams per square meter, obtained from Fiberweb Corporation, Old Hickory, Tenn., USA) and drying in an oven at 70° C.

Example 6

Example 6 was run in the same manner as Example 5 except that 10 grams of particles from Example 4 were added to 5 grams of the dispersion of silane terminated polyurethanes and 4 grams of water.

Example 7

*Pseudomonas aeruginosa* (obtained from American Type Culture Collection, strain number 15442) was grown to stationary phase overnight in tryptic soy broth at 37° C. Then the cultures were diluted 1 to 10,000 in sterile phosphate-buffered saline and 10 microliters of the diluted suspension was placed in a single drop onto polycarbonate membranes (25 millimeter diameter, 0.2 micrometer pore size, polycarbonate filter membranes obtained from Whatman, Kent, United Kingdom) placed on top of tryptic soy agar (TSA) containing 1.5 percent agar. The bacteria were allowed to grow for 24 hours at 37° C. After the growth period, the filters were aseptically transferred to TSA poured into sterile, polystyrene, 6-well plates.

Example 1 and Example 2 particles were each loaded with PHMB by mixing 2 parts by weight of 0.25 weight percent PHMB solution (in water) to 1 part by weight polymeric particles in a glass jar before drying overnight at 40° C. 100 milligrams each of resulting PHMB-loaded particles of Example 1, Example 2, and as-prepared (i.e., free of PHMB) Example 1 and Example 2 particles were placed on top of bacteria to completely cover the bacteria and 200 microliter of sterile, deionized water was pipetted on top of the particles. The particle-covered bacteria were then incubated for 18 hours at 37° C. Each sample of polymeric particles was tested in triplicate. The membranes covered in bacteria and polymeric particles were then transferred into 10 milliliters of Letheen neutralizing broth containing 7 grams/liter of added lecithin. The samples were mixed on a vortex mixer at maximum speed for 1 minute and then sonicated for 1 minute in a sonicating water bath (Model 2150 from Branson Ultrasonics Corporation, Danbury, Conn., USA). The samples were then serially diluted 10-fold in Letheen broth containing 7 grams/liter of lecithin and samples were plated onto AC Petrifilm obtained from 3M, St. Paul, Minn. under trade designation "3M PETRIFILM Aerobic Count Plates". The 3M PETRIFILM plates were incubated for 48 hours at 37° C., the number of surviving colony forming units (CFU) were enumerated, and the average log reduction was calculated by subtracting the log (CFU/sample) of the PHMB-treated particle from the surviving log (CFU/sample) of the corresponding PHMB-free particles. Results are shown in table 2.

TABLE 2

Characterization of anti-bacterial properties

| Description of treatment | Average log reduction of surviving bacteria |
|---|---|
| PHMB-loaded Example 1 particles | 2.11 |
| PHMB-loaded Example 2 particles | 1.88 |

Example 8

The article described in Example 5 was cut into 10 millimeter disks with a die punch and loaded with PHMB using a 0.25% PHMB solution (in water) so that the final concentration of PHMB was 0.5% (final weight of PHMB/total weight of the disk). *Pseudomonas aeruginosa* was grown on membrane filters as described in Example 7 and the PHMB-loaded disks of the article, as well as PHMB-free discs were each wet with 50 microliters of sterile water and placed on top of the bacteria in stacks of 5 disks. After incubation at 37° C. for 18 hours, the membranes covered in bacteria and disks of material were transferred to 10 milliliters of Letheen neutralizing broth containing 7 grams/liter of lecithin and surviving bacteria were enumerated as described in Example 7. PHMB-loaded Example 6 material reduced the number of surviving bacteria by 1.45 log (CFU/sample).

Example 9

The Example 9 polymeric particles were synthesized as described in Example 1 except that the second phase contained 100 grams of SR 603OP, 5 grams of a 75 weight percent solution of (3-acrylamido-propyl)trimethyl ammonium chloride, 5 grams glycerol dimethacrylate, 43 grams of PPG, and 250 milligrams of IRGACURE 819.

Example 10

The Example 10 polymeric particles were synthesized as described in Example 1 except that the second phase contained 45 grams SR 339, 45 grams SR 603OP, 10 grams 2-carboxyethyl acrylate, 43 grams PPG, and 250 milligrams IRGACURE 819.

Example 11

The Example 11 polymeric particles were synthesized as described in Example 1 except that the second phase contained 45 grams SR 339, 45 grams SR 603OP, 10 grams 2-hydroxyethyl methacrylate, 43 grams PPG, and 250 milligrams IRGACURE 819.

What is claimed is:

1. A reaction mixture comprising:
   a) a first phase comprising
      i) a compound of Formula (I)
      $$HO[-CH_2-CH(OH)-CH_2-O]_n-H \quad (I)$$
      wherein n is an integer equal to at least 1; and
      ii) a nonionic surfactant; and
   b) a second phase dispersed in the first phase, wherein a volume of the first phase is greater than a volume of the second phase and wherein the second phase comprises
      i) a monomer composition comprising a monomer of Formula (II)
      $$CH_2=C(R^1)-(CO)-O[-CH_2-CH_2-O]_p-(CO)-C(R^1)=CH_2 \quad (II)$$
      wherein
      p is an integer equal to at least 1;
      $R^1$ is hydrogen or alkyl; and
      ii) a polypropylene glycol) having a weight average molecular weight of at least 500 grams/mole.

2. The reaction mixture of claim 1, wherein the monomer composition further comprises a second monomer having one (meth)acryloyl group.

3. The reaction mixture of claim 2, wherein the second monomer comprises a hydroxyl-containing monomer.

4. The reaction mixture of claim 2, wherein the second monomer comprises a sulfonyl-containing monomer.

5. The reaction mixture of claim 2, wherein the second monomer is of Formula (III)
$$CH_2=CR^1-(CO)-O-Y-R^2 \quad (III)$$
wherein
   $R^1$ is hydrogen or methyl;
   Y is a single bond, alkylene, oxyalkylene, or poly(oxyalkylene); and
   $R^2$ is a carbocyclic group or heterocyclic group.

* * * * *